United States Patent
Noble et al.

(10) Patent No.: US 10,821,284 B2
(45) Date of Patent: *Nov. 3, 2020

(54) CURRENT STEERING COMPATIBLE IMAGE-GUIDED COCHLEAR IMPLANT ELECTRODE DEACTIVATION METHODS AND APPLICATIONS OF SAME

(71) Applicant: Vanderbilt University, Nashville, TN (US)

(72) Inventors: Jack Noble, Nashville, TN (US); Rene H. Gifford, Franklin, TN (US); Robert F. Labadie, Nashville, TN (US); Benoit M. Dawant, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 185 days.

This patent is subject to a terminal disclaimer.

(21) Appl. No.: 15/770,260

(22) PCT Filed: Oct. 27, 2016

(86) PCT No.: PCT/US2016/059123
§ 371 (c)(1),
(2) Date: Apr. 23, 2018

(87) PCT Pub. No.: WO2017/075219
PCT Pub. Date: May 4, 2017

(65) Prior Publication Data
US 2018/0311501 A1    Nov. 1, 2018

Related U.S. Application Data

(63) Continuation-in-part of application No. 14/390,503, filed as application No. PCT/US2013/035076 on Apr. 3, 2013, now Pat. No. 9,572,981.
(Continued)

(51) Int. Cl.
*A61B 5/12* (2006.01)
*A61N 1/36* (2006.01)
(Continued)

(52) U.S. Cl.
CPC ............ *A61N 1/36039* (2017.08); *A61B 5/12* (2013.01); *A61B 5/4848* (2013.01); *A61B 6/03* (2013.01);
(Continued)

(58) Field of Classification Search
CPC .... A61N 1/36039; A61N 1/0541; A61B 6/12; A61B 6/03; A61B 5/12; A61B 5/4848; A61B 34/20
See application file for complete search history.

(56) References Cited

U.S. PATENT DOCUMENTS 8,126,565 B1    2/2012  Litvak et al.
2007/0293785 A1  12/2007  Litvak
(Continued)

OTHER PUBLICATIONS

Korean Intellectual Property Office (ISR/KR), "International Search Report for PCT/US2016/059123", Korea, dated Feb. 16, 2017.
(Continued)

*Primary Examiner* — Rex R Holmes
(74) *Attorney, Agent, or Firm* — Locke Lord LLP; Tim Tingkang Xia, Esq.

(57) ABSTRACT

Systems and methods for performing current steering compatible image-guided cochlear implant (CI) electrode deactivation. The cochlear implant includes an electrode array having a plurality of electrodes implanted in a cochlea of a living subject. For each electrode, a corresponding distance-vs-frequency (DVF) curve is obtained. An analysis is performed on the DVF curves to identify the interfering electrodes, each having an interference with at least one other electrode. Then, rules may apply to the interfering electrodes
(Continued)

in order to select one or more interfering electrodes to be deactivated. The rules may include: keeping the electrode having a corresponding DVF curve located at a left-most location on the plot to avoid a resulting sound frequency upshift; avoiding leaving any electrode stranded without a neighboring electrode; and deactivating a minimal number of the interfering electrodes to ensure that high interference is allowed only for each electrode with one neighboring electrode.

20 Claims, 12 Drawing Sheets

Related U.S. Application Data

(60) Provisional application No. 62/247,012, filed on Oct. 27, 2015, provisional application No. 61/619,824, filed on Apr. 3, 2012.

(51) Int. Cl.
  *A61B 34/20*   (2016.01)
  *A61N 1/05*   (2006.01)
  *A61B 6/12*   (2006.01)
  *A61B 6/03*   (2006.01)
  *A61B 5/00*   (2006.01)

(52) U.S. Cl.
  CPC .......... *A61B 6/12* (2013.01); *A61B 34/20* (2016.02); *A61N 1/0541* (2013.01)

(56) References Cited

U.S. PATENT DOCUMENTS

| | | |
|---|---|---|
| 2015/0025596 A1 | 1/2015 | Kals |
| 2015/0088225 A1 | 3/2015 | Noble et al. |
| 2015/0112408 A1 | 4/2015 | Kals |

OTHER PUBLICATIONS

National Institute on Deafness and Other Communication Disorders, "Cochlear Implants," No. 11-4798, 2014.
Buss E, Pillsbury HC, Buchman CA, Pillsbury CH, Clark MS, Haynes DS, Labadie RF, Amberg S, Roland PS, Kruger P, Novak MA, Wirth JA, Black JM, Peters R, Lake J, Wackym PA, Firszt JB, Wilson BS, Lawson DT, Schatzer R, S. DHP, Barco AL: Multicenter U.S. Bilateral med-el cochlear implantation study: Speech perception over the first year of use. Ear Hear 2008;29:20-32.
Dorman MF, Yost W, Wilson BS, Gifford RH: Speech perception and sound localization by adults with bilateral cochlear implants. Seminars in Hearing 2009;32:73-89.
Gifford RH, Shallop JK, Peterson AM (2008). Speech Recognition Materials and Ceiling Effects: Considerations for Cochlear Implant Programs. Audiol Neurotol, 13:193-205.
Gifford RH, Dorman MF, Sheffield SW, Teece K, Olund AP. "Availability of binaural cues for bilateral cochlear implant recipients and bimodal listeners with and without hearing preservation." Audiol Neurotol. 2014;19(1):57-71.
Litovsky RY, Parkinson A, Arcaroli J, Sammeth C: Simultaneous bilateral cochlear implantation in adults: A multicenter clinical study. Ear Hear 2006;27:714-730.
Holden LK, Finley CC, Firszt JB, Holden TA, Brenner C, Potts LG, Gotter BD, Vanderhoof SS, Mispagel K, Heydebrand G, Skinner MW, "Factors affecting open-set word recognition in adults with cochlear implants," Ear Hear. 34(3):342-60, 2013.
Wanna, G.B., Noble J.H., Carlson, M.L., Gifford, R.H., Dietrich, M.S., Haynes, D.S. Dawant, B.M., and Labadie, R.F., "Impact of Electrode Design and Surgical Approach on Scalar Location and Cochlear Implant Outcomes," Laryngoscope, vol. 124(S6), pp. S1-S7, 2014.
Wanna GB, Noble JH, Gifford RH, Dietrich MS, Sweeney AD, Zhang D, Dawant BM, Rivas A, Labadie RF. "Impact of Intrascalar Electrode Location, Electrode Type, and Angular Insertion Depth on Residual Hearing in Cochlear Implant Patients: Preliminary Results." Otol Neurotol. 36(8):1343-8, 2015.
Stakhovskaya O, Spridhar D, Bonham BH, Leake PA. Frequency Map for the Human Cochlear Spiral Ganglion: Implications for Cochlear Implants. Journ. Assoc. Res. Otol. 8, 2007. : 220-233.
Noble JH, Labadie RF, Gifford RH, Dawant BM, "Image-guidance enables new methods for customizing cochlear Implant stimulation strategies," IEEE Trans Neural Syst Rehabil Eng. vol. 21(5):820-9, 2013.
Noble JH, Gifford RH, Hedley-Williams AJ, Dawant BM, and , Labadie RF, "Clinical evaluation of an image-guided cochlear implant programming strategy," Audiology & Neurotology, vol. 19, pp. 400-411, 2014.
Koch DB1, Quick A, Osberger MJ, Saoji A, Litvak L. "Enhanced hearing in noise for cochlear implant recipients: clinical trial results for a commercially available speech-enhancement strategy." Otol Neurotol. Jun. 2014;35(5):803-9.
Folstein MF, Folstein SE, McHugh PR. Mini-mental state. A practical method for grading the cognitive state of patients for the clinician. J Psychiatr Res 1975;12:189-198.
Gifford RH, Hedley-Williams A, Spahr AJ. Clinical assessment of spectral modulation detection for cochlear implant recipients: a non-language 480 based measure of performance outcomes. Int J Audiol 2014;53(3):159-64.
Peterson GE, Lehiste I. (1962). Revised CNC lists for auditory tests. J Speech Hear Disord. 27:62-70.
Spahr A.J., Dorman M.F., Litvak L.M., Van Wie S., Gifford R.H., Loizou P.C., Loiselle L.M., Oakes T., Cook S., "Development and validation of the AzBio sentence lists," Ear Hear. 33(1): 112-7, 2012.
MSTB: The New Minimum Speech Test Battery for Adult Cochlear Implant Users. Available at: http://auditorypotential.com/MSTB.html. Accessed Dec. 10, 2015.
Bench J., Kowal A., Bamford J., "The BKB (Bamford-Kowal-Bench) sentences lists for partially-hearing children," Br. J. Audiol. 13: 108-12, 1979.
Litvak LM, Spahr AJ, Saoji AA, Fridman GY. Relationship between perception of spectral ripple and speech recognition in cochlear implant and vocoder listeners. J Acoust Soc Am 2007;122: 982-991.
Saoji AA, Litvak LM, Spahr AJ, Eddins DA. Spectral modulation detection and vowel and consonant identifications in cochlear implant listeners. J Acoust Soc Am 2009;126 (3): 955-8.
Thornton AR, Raffin MJ. Speech-discrimination scores modeled as a binomial variable. J Speech Hear Res 1978;21:507-518.

CURRENT STEERING COMPATIBLE IMAGE-GUIDED COCHLEAR IMPLANT ELECTRODE DEACTIVATION METHODS AND APPLICATIONS OF SAME

CROSS-REFERENCE TO RELATED PATENT APPLICATION

This application is a national stage entry of PCT application Serial No. PCT/US2016/059123, filed Oct. 27, 2016, which claims priority to and the benefit of U.S. provisional patent application Ser. No. 62/247,012, filed Oct. 27, 2015 and is a continuation-in-part of U.S. patent application Ser. No. 14/390,503, filed Oct. 3, 2014, now U.S. Pat. No. 9,572,981, which is a national stage entry of PCT application Serial No. PCT/US2013/035076, filed Apr. 3, 2013, which itself claims priority to and the benefit of, U.S. provisional patent application Ser. No. 61/619,824, filed on Apr. 3, 2012, All of the above disclosures are incorporated herein by reference in their entireties.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [11] represents the tenth reference cited in the reference list, namely, Noble J H, Labadie R F, Gifford. R H, Dawant B M, "Image-guidance enables new methods for customizing cochlear implant stimulation strategies," IEEE Trans Neural Syst Rehabil Eng. vol. 21(5): 820-9, 2013.

STATEMENT AS TO RIGHTS UNDER FEDERALLY-SPONSORED RESEARCH

This invention was made with government support under grant number DC014037 awarded by the National Institutes of Health. The government has certain rights in the invention.

FIELD OF THE INVENTION

The present invention relates generally to cochlear implant (CI) image processing technology, and more particularly to systems and methods for performing current steering compatible image-guided CI electrode deactivation, and applications thereof.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Cochlear implants (CIs) are neural prosthetics used to treat severe to profound hearing loss. As of 2012, over 320,000 devices have been implanted worldwide [1]. CIs use an array of electrodes implanted into the cochlea to directly stimulate spiral ganglion (SG) neurons to induce hearing sensation. Implants available today produce remarkable results for the vast majority of recipients, with average word recognition of 60% and 70% for unilateral and bilateral recipients, respectively [2-6]. Despite this success, a significant number of users receive marginal benefit, and restoration to normal fidelity is rare even among the best performers.

The intra-cochlear positioning of the electrode array is a factor known to affect outcomes [7-9]. Electrode positioning can influence the neural stimulation pattern overlap across electrodes, which arises due to the non-selective nature of electrical stimulation relative to natural hearing and can affect speech recognition. In natural hearing, a nerve pathway is activated when the characteristic frequency (CF) associated with that pathway is present in the incoming sound. Normal-hearing individuals have approximately 30,000 neural fibers. Neural pathways are tonotopically ordered by decreasing CF along the length of the cochlear duct, and this finely tuned spatial organization is well known [10]. CIs cannot reproduce the selective activation of specific neural regions that occurs naturally. Rather, electrical stimulation creates broad excitation patterns. When the array is placed farther away from the neural regions, broader excitation patterns are created. Broader excitation patterns create more excitation overlap, or "interference," with neighboring electrodes. More spectral smearing occurs with greater channel interference, leading to poorer speech recognition in quiet and in noise.

Therefore, a heretofore unaddressed need exists in the art to address the aforementioned deficiencies and inadequacies.

SUMMARY OF THE INVENTION

One aspect of the present invention relates to a method for performing current steering compatible image-guided cochlear implant (CI) electrode deactivation. In certain embodiments, the method includes: obtaining, for a plurality of electrodes of an electrode array implanted in a cochlea of a living subject, a plurality of distance-vs-frequency (DVF) curves, where each of the DVF curves corresponds to one of the electrodes; performing an analysis on the DVF curves to identify a plurality of interfering electrodes from the electrodes, where each of the interfering electrodes has an interference with at least one other electrode; and selecting and deactivating, based on a plurality of rules, at least one of the interfering electrodes.

In certain embodiments, the DVF curves are provided on a plot to visualize distances of the electrodes from a modiolus of the living subject, wherein the plot has a horizontal axis showing an angular depth and a characteristic frequency (CF) of the neural regions, and a vertical axis showing a distance from the electrodes to corresponding spiral ganglion stimulation sites.

In certain embodiments, the interfering electrodes are identified from the electrodes based on positions of the electrodes relative to neural regions of the living subject stimulated by the electrodes, and an overlapping degree of each of the corresponding neural regions of the electrodes, where each of the electrodes corresponds to one of the neural regions. In certain embodiments, the positions of the electrodes relative to the neural regions interfering electrodes are determined by locations of the DVF curves on the vertical axis of the plot, where for each of the electrodes, the position of the electrode is farther from the corresponding neural region when the corresponding DVF curve of the electrode is higher on the plot. In certain embodiments, the overlapping degree of each of the corresponding neural regions of the electrodes is estimated by depths of concavity between the DVF curves on the plot, wherein for each of the DVF curves, the overlapping degree is high when the DVF curve has little to no depth of concavity with neighboring DVF curves on the plot.

In certain embodiments, the rules include: keeping the electrode having a corresponding DVF curve located at a left-most location on the plot to avoid a resulting sound frequency upshift; avoiding leaving any of the electrodes stranded without a neighboring electrode; and deactivating a minimal number of the interfering electrodes to ensure that high interference is allowed only for each of the electrodes with one of the neighboring electrodes.

Another aspect of the present invention relates to a system for performing current steering compatible image-guided CI electrode deactivation. In certain embodiments, the system includes: a CI device being implanted in a cochlea of a living subject, the CI device comprising an electrode array having a plurality of electrodes; and at least one computing device having one or more processors and a storage device storing computer executable code. The computer executable code, when executed at the one or more processors, is configured to perform functions including: obtaining, for a plurality of electrodes of an electrode array implanted in a cochlea of a living subject, a plurality of distance-vs-frequency (DVF) curves, where each of the DVF curves corresponds to one of the electrodes; performing an analysis on the DVF curves to identify a plurality of interfering electrodes from the electrodes, where each of the interfering electrodes has an interference with at least one other electrode; and selecting and deactivating, based on a plurality of rules, at least one of the interfering electrodes.

In certain embodiments, the functions further include: providing the DVF curves on a plot to visualize distances of the electrodes from a modiolus of the living subject, wherein the plot has a horizontal axis showing an angular depth and a characteristic frequency of the neural regions, and a vertical axis showing a distance from the electrodes to corresponding spiral ganglion stimulation sites.

In certain embodiments, the interfering electrodes are identified from the electrodes based on positions of the electrodes relative to neural regions of the living subject stimulated by the electrodes, and an overlapping degree of each of the corresponding neural regions of the electrodes, where each of the electrodes corresponds to one of the neural regions. In certain embodiments, the positions of the electrodes relative to the neural regions interfering electrodes are determined by locations of the DVF curves on the vertical axis of the plot, where for each of the electrodes, the position of the electrode is farther from the corresponding neural region when the corresponding DVF curve of the electrode is higher on the plot. In certain embodiments, the overlapping degree of each of the corresponding neural regions of the electrodes is estimated by depths of concavity between the DVF curves on the plot, wherein for each of the DVF curves, the overlapping degree is high when the DVF curve has little to no depth of concavity with neighboring DVF curves on the plot.

In certain embodiments, the rules include: keeping the electrode having a corresponding DVF curve located at a left-most location on the plot to avoid a resulting sound frequency upshift; avoiding leaving any of the electrodes stranded without a neighboring electrode; and deactivating a minimal number of the interfering electrodes to ensure that high interference is allowed only for each of the electrodes with one of the neighboring electrodes.

In certain embodiments, the rules are codified into a cost function that permits assigning a quantitative quality score to a given active electrode set. In certain embodiments, the active electrode set is determined using an exhaustive search scheme where all possible combinations of active electrodes are evaluated to find the active electrode set that satisfies the rules, where the degree to which each possible active electrode set satisfies the rules is quantified using a cost function.

A further aspect of the present invention relates to a non-transitory computer-readable medium storing computer executable code. The computer executable code, when executed at one or more processors, causes a system to perform functions for performing current steering compatible image-guided cochlear implant (CI) electrode deactivation. In certain embodiments, the functions include: (a) obtaining, for a plurality of electrodes of an electrode array implanted in a cochlea of a living subject, a plurality of distance-vs-frequency (DVF) curves, where each of the DVF curves corresponds to one of the electrodes; (b) performing an analysis on the DVF curves to identify a plurality of interfering electrodes from the electrodes, where each of the interfering electrodes has an interference with at least one other electrode; and (c) selecting and deactivating, based on a plurality of rules, at least one of the interfering electrodes.

Certain aspects of the present invention relate to a method for customizing cochlear implant stimulation of a living subject using a current steering compatible image-guided cochlear implant programming (IGCIP) strategy, which includes: configuring a plurality of electrodes of an electrode array implanted in a cochlea of the living subject using the method or the system as described above.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
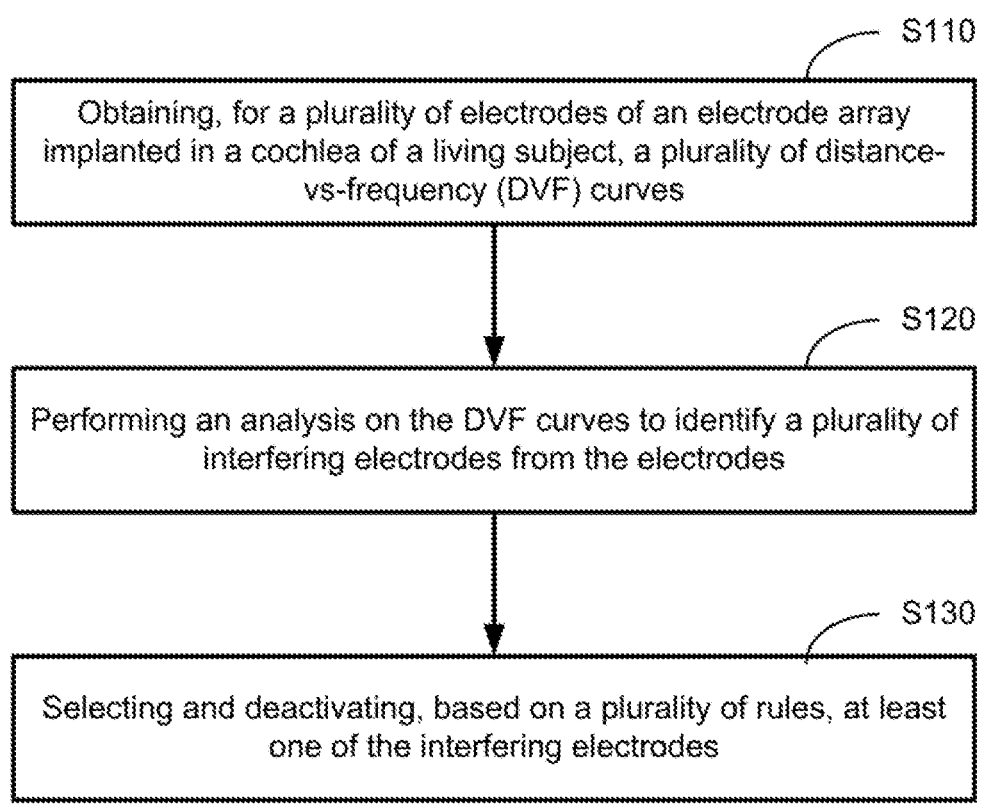
FIG. 1 shows a flowchart of a method for performing current steering compatible image-guided CI electrode deactivation according to certain embodiments of the present invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the phrase "at least one of A, B, and C" should be construed to mean a logical (A or B or C), using a non-exclusive logical OR. It should be understood that one or more operations within a method is executed in different order (or concurrently) without altering the principles of the invention.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to systems and methods for performing current steering compatible image-guided cochlear implant (CI) electrode deactivation, and applications thereof.

Existing methods were proposed to localize CI electrodes relative to the sites they stimulate inside the cochlea. For example, the previous method for selecting channels to deactivate assumed the stimulation strategy being used was the standard "continuous interleaved sampling" (CIS) strategy. In this strategy, individual electrodes are fired independently in a non-simultaneous manner. With "current steering" strategies, adjacent electrodes are fired simultaneously to attempt to create a peak neural activation region at neural cells that lie between the two electrodes. One issue with deactivating channels is that if both of an electrode's neighboring electrodes are deactivated, or if the lone neighbor of an end electrode is deactivated, steering must be turned off and the map must be returned to CIS to keep that electrode active. The previous deactivation method would in general result in recommended electrode configurations that had electrodes with no neighbors, making it incompatible with current steering. To overcome this problem, a new strategy is proposed to select electrodes to deactivate to reduce channel interaction artifacts in a way that accounts for steering does not result electrodes that are "stranded" without neighbors for steering.

Methods have been proposed to localize CI electrodes relative to the sites they stimulate inside the cochlea [11]. With this imaging information, a pruned electrode set can be chosen so that the subset electrodes that are active will stimulate more discrete neural populations, and this process, known as image-guided cochlear implant programming (IG-CIP), has been shown to lead to significant improvements in speech understanding in quiet and in noise as well as improved spectral resolution over a standard all-on approach [12]. In that work, current steering was deactivated to allow for selective deactivation of individual electrodes without consideration of paired stimulation. However, paired electrode stimulation has been shown to improve battery life and is required for the use of a proprietary noise reduction algorithm (ClearVoice™) that has been shown to improve hearing in noise in Advanced Bionics CI users [13]. The noise reduction algorithm estimates the signal-to-noise ratio (SNR) in each channel. For those channels in which poor SNR is identified, channel gain is reduced. Therefore, certain embodiments of the present invention relate to an image-guided electrode selection strategy that allows for the use of current steering.

In certain aspects, this invention relates to a method for selection of cochlear implant channels that is compatible with current steering-based cochlear implant stimulation strategies. It is based on a previously disclosed method for image-guided selection of cochlear implant channels. In certain embodiments, the method includes: (1) using image analysis techniques being developed to accurately locate the position of implanted cochlear implant electrodes relative to the nerves they stimulate; (2) based on the known electrode position, estimating the neural stimulation region for each electrode and the degree of overlap of neural stimulation regions between electrodes; and (3) finding channels that have a high degree of overlap and deactivate them from the patient's map. Among other things, the method leads to improved hearing outcomes because high channel overlap creates channel interaction artifacts that are known to negatively affect outcomes. The novel invention here is a new method for selecting which channels to deactivate to reduce channel interaction artifacts. The new strategy deactivates channels in patterns that are constrained to be compatible with the "current steering" stimulation strategies.

In certain embodiments, the method for interpreting the position of the electrodes within the cochlea to determine which electrodes should be deactivated for a current steering stimulation strategy is novel. The new method is to evaluate whether the set of steered channels, each of which comprises two neighboring electrodes, is subject to too much stimulation overlap and channel interaction. Channels composed of electrodes that are more distant to the neural stimulation sites are assumed to have greater spread of excitation. All channels composed of electrodes that sit in the immediate vicinity of neural sites are assumed to not create channel interaction and are left active. Other electrodes are selected for deactivation in order to ensure that channels composed of distant electrodes do not interfere. Interference is determined using the electrode distance vs frequency curve analysis technique proposed for the previous invention where steering was not accounted for.

One aspect of the present invention relates to a method for performing current steering compatible image-guided cochlear implant (CI) electrode deactivation. In certain embodiments, the method includes: obtaining, for a plurality of electrodes of an electrode array implanted in a cochlea of a living subject, a plurality of distance-vs-frequency (DVF) curves, where each of the DVF curves corresponds to one of the electrodes; performing an analysis on the DVF curves to identify a plurality of interfering electrodes from the electrodes, where each of the interfering electrodes has an interference with at least one other electrode; and selecting and deactivating, based on a plurality of rules, at least one of the interfering electrodes.

Another aspect of the present invention relates to a system for performing current steering compatible image-guided CI electrode deactivation. In certain embodiments, the system includes: a CI device being implanted in a cochlea of a living subject, the CI device comprising an electrode array having a plurality of electrodes; and at least one computing device having one or more processors and a storage device storing computer executable code. The computer executable code, when executed at the one or more processors, is configured to perform functions including: obtaining, for a plurality of electrodes of an electrode array implanted in a cochlea of a living subject, a plurality of distance-vs-frequency (DVF) curves, where each of the DVF curves corresponds to one of the electrodes; performing an analysis on the DVF curves to identify a plurality of interfering electrodes from the electrodes, where each of the interfering electrodes has an interference with at least one other electrode; and selecting and deactivating, based on a plurality of rules, at least one of the interfering electrodes.

In certain aspects, the invention relates to software that implements the invention to recommend a current steering electrode configuration for cochlear implant recipients or the know-how of how to interpret the position of the electrodes in the cochlea to determine which electrodes should be deactivated for a current steering stimulation strategy.

These and other aspects of the present invention are further described below.

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

FIG. 1 shows a flowchart of a method for performing current steering compatible image-guided CI electrode deactivation according to certain embodiments of the present invention. It should be particularly noted that, unless otherwise stated in the present disclosure, the steps of the method may be arranged in a different sequential order, and are thus not limited to the sequential order as shown in FIG. 1.

As shown in FIG. 1, in step S110, a plurality of distance-vs-frequency (DVF) curves may be obtained for a plurality of electrodes of an electrode array implanted in a cochlea of a living subject. In certain embodiments, the DVF curves may be obtained using a system having at least one computing devices with necessary software applications that may be used to perform the IGCIP. In step S120, an analysis is performed on the DVF curves to identify a plurality of interfering electrodes from the electrodes. Then, in step S130, at least one of the interfering electrodes may be selected and deactivated based on a plurality of rules. In certain embodiments, the rules include: keeping the electrode having a corresponding DVF curve located at a left-most location on the plot to avoid a resulting sound frequency upshift; avoiding leaving any of the electrodes stranded without a neighboring electrode; and deactivating a minimal number of the interfering electrodes to ensure that high interference is allowed only for each of the electrodes with one of the neighboring electrodes.

In certain embodiments, the rules may be codified into a cost function that permits assigning a quantitative quality score to a given active electrode set. In certain embodiments, the active electrode set may be determined using an exhaustive search scheme where all possible combinations of active electrodes are evaluated to find the active electrode set that satisfies the rules, where the degree to which each possible active electrode set satisfies the rules is quantified using the quantitative quality score assigned by the cost function.

In order to show that the new strategies may be more effective than the current strategies employed in the cochlear implants, the inventors have conducted the following experiments as described below.

Experiment One

Certain embodiments of the method are tested in cochlear implant subjects. In the following experiment, two subjects have undergone remapping with the experimental settings.
Patient #1

Figure 2:
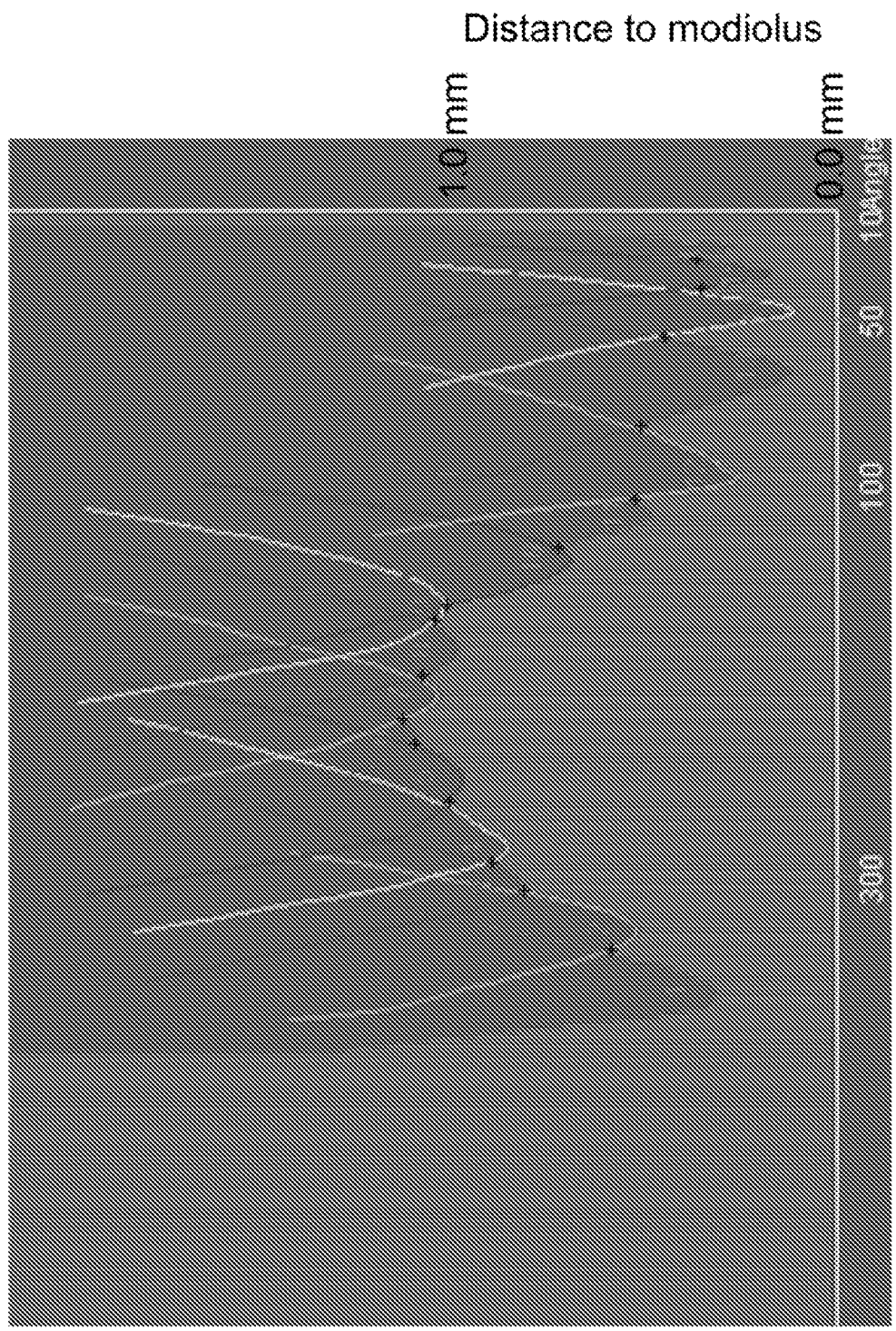
FIG. 2 schematically shows a plot of raw DVF curves obtained from a patient according to certain embodiments of the present invention.

In the experiment for patient #1, a cochlear implant device having an electrode array with 16 electrodes is used to obtain the raw DVF curves, as shown in FIG. 2. Specifically, FIG. 2 schematically shows a plot of raw DVF curves obtained from a patient according to certain embodiments of the present invention. In particular, the plot is used to visualize distances of the electrodes from a modiolus of the living subject. As shown in FIG. 2, the plot has a horizontal axis showing an angular depth and a characteristic frequency (CF) of the neural regions, and a vertical axis showing a distance from the electrodes to corresponding spiral ganglion stimulation sites of the patient. In other words, for each of the DVF curves corresponding to the electrodes #1-16, the DVF curve defines the distance from the electrode to the neural sites on the modiolus of the patient.

Figure 3:
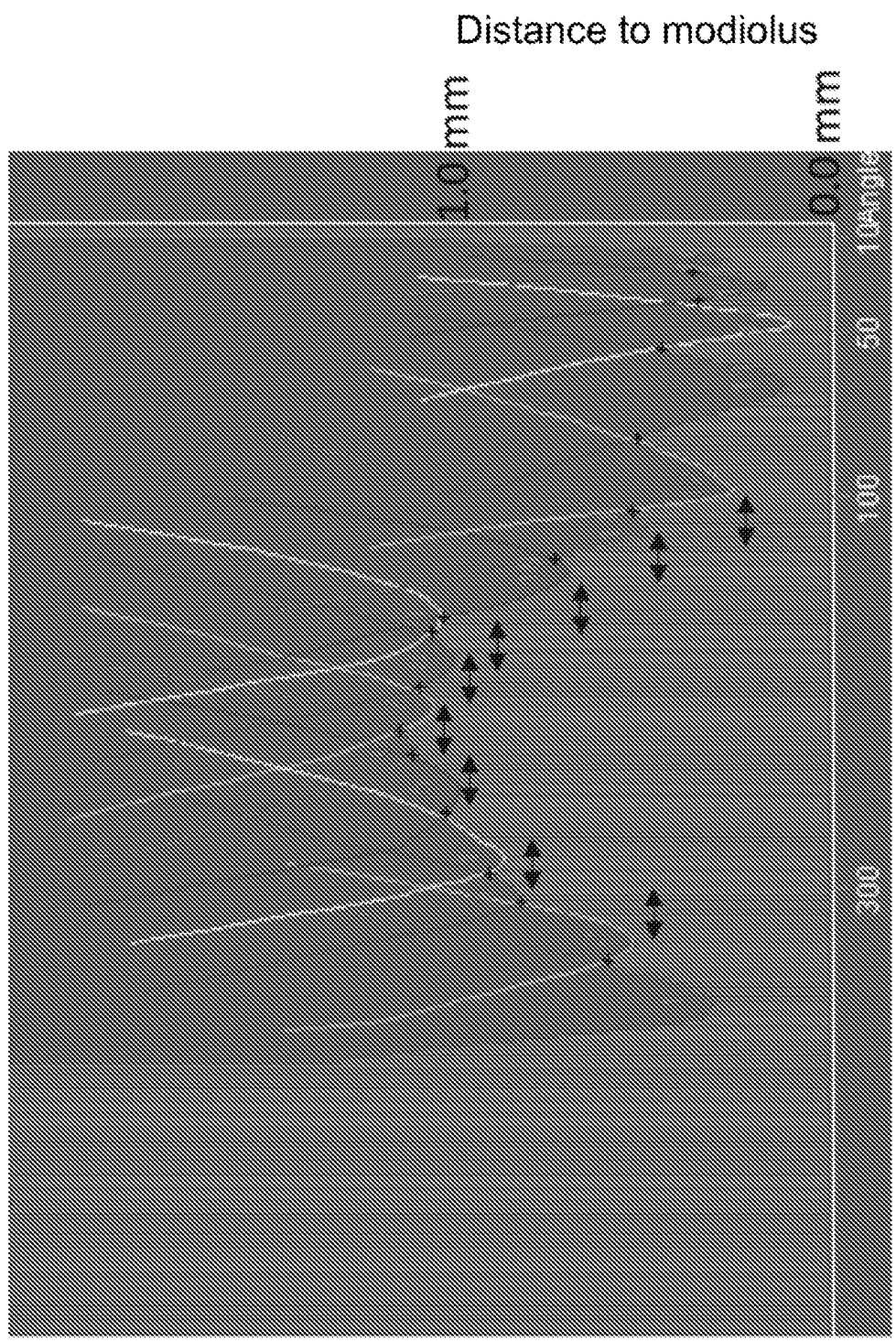
FIG. 3 schematically shows a plot of the DVF curves as shown in FIG. 2 being processed to identify the neighboring electrodes having high interferences according to certain embodiments of the present invention.

FIG. 3 schematically shows a plot of the DVF curves as shown in FIG. 2 being processed to identify the neighboring electrodes having high interferences according to certain embodiments of the present invention. In particular, interference between neighboring electrodes is identified for electrodes that are farther from the modiolus (higher in the plot) and have curves that have a high degree of overlap (little or no depth of concavity) with their neighbors. This indicates that the two electrodes are equally close to the same neural sites and thus likely stimulating the same neural sites, i.e., "interacting." For example, as shown in FIG. 3, the neighboring electrodes #6 and #7 may be determined to have high interference, and thus be identified as the interfering electrodes.

Figure 4:
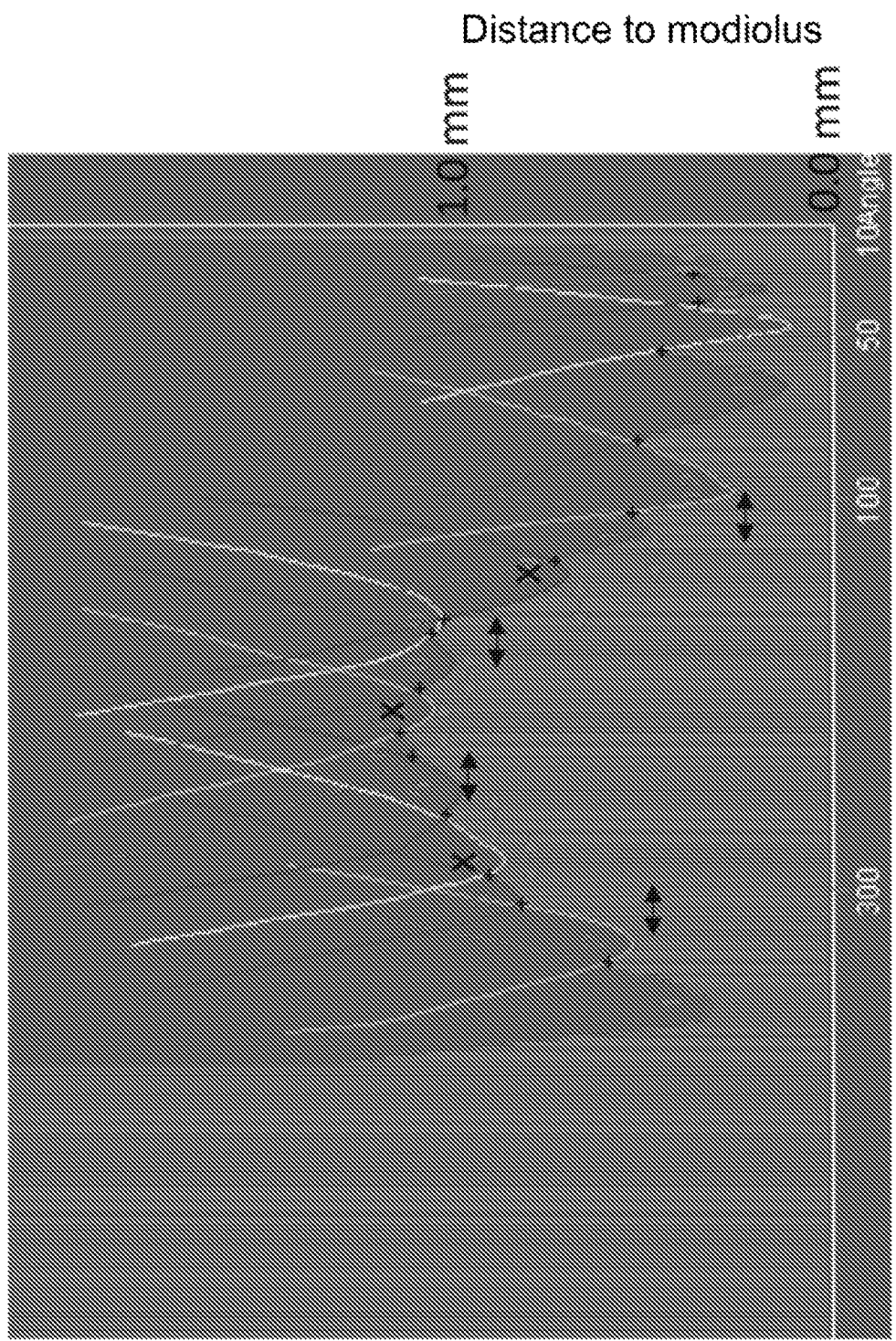
FIG. 4 schematically shows a plot of the DVF curves as shown in FIG. 2 being processed to select the interfering electrodes to be deactivated according to certain embodiments of the present invention.

Once the interfering electrodes are identified, the rules may be applied to select at least one of the interfering electrodes to be deactivated. FIG. 4 schematically shows a plot of the DVF curves as shown in FIG. 2 being processed to select the interfering electrodes to be deactivated according to certain embodiments of the present invention. In certain embodiments, the rules may include:
  1. keeping the electrode having a corresponding DVF curve located at a left-most location on the plot to avoid a resulting sound frequency upshift;
  2. avoiding leaving any of the electrodes stranded without a neighboring electrode; and 3. deactivating a minimal number of the interfering electrodes to ensure that high interference is allowed only for each of the electrodes with one of the neighboring electrodes.

Figure 5:
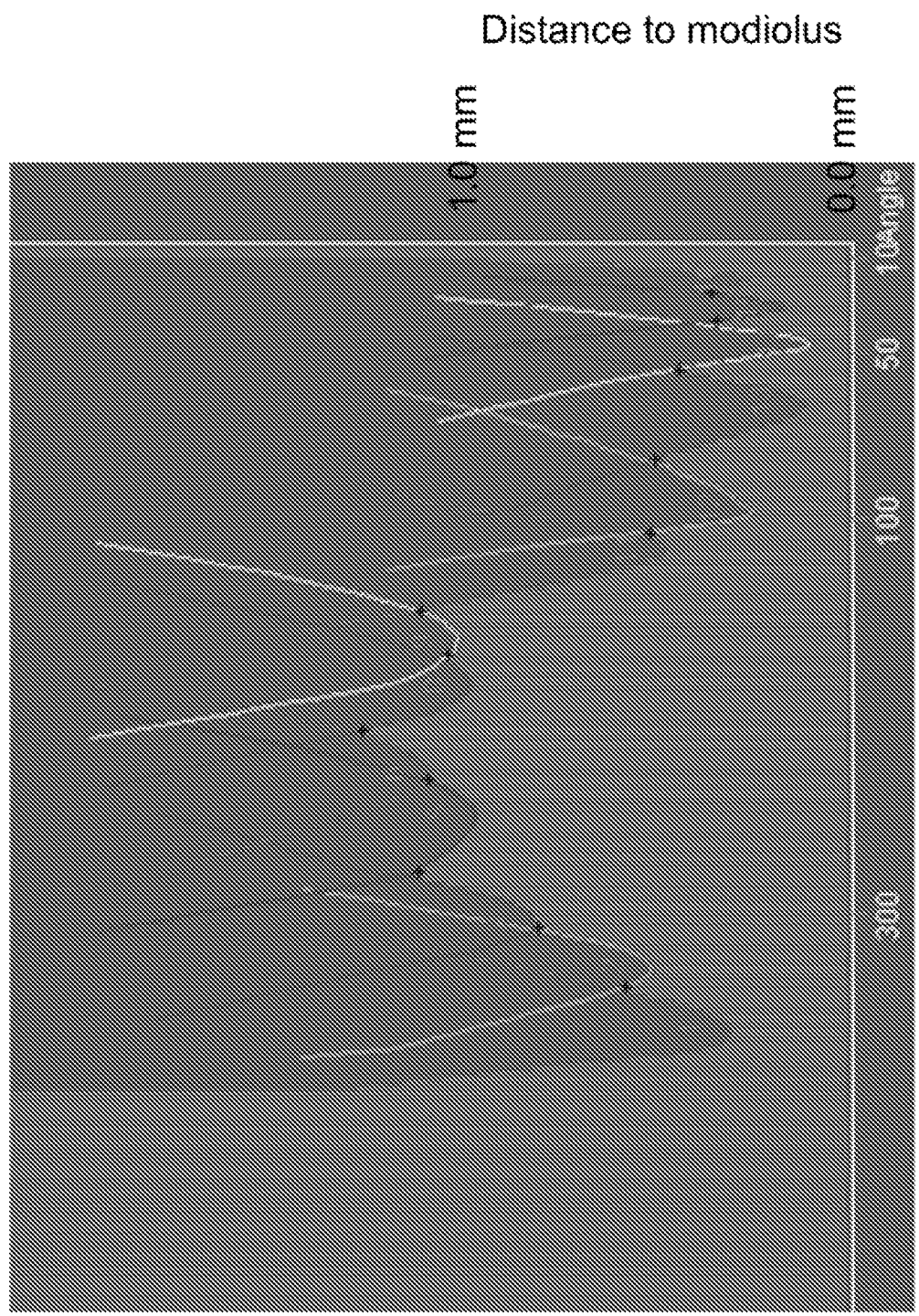
FIG. 5 schematically shows a plot of the DVF curves after deactivating the selected interfering electrodes as shown in FIG. 4 according to certain embodiments of the present invention.

As both neighbors represent a "steered" channel, the third rule ensures that two neighboring steered channels do not have high interference with each other. As shown in FIG. 4, by applying the rules, the electrodes #4, #7 and #10 were selected to be deactivated. This removes the steered channels shown in red above. FIG. 5 schematically shows a plot of the DVF curves after deactivating the selected interfering electrodes as shown in FIG. 4 according to certain embodiments of the present invention.

Patient #2

Figure 6:
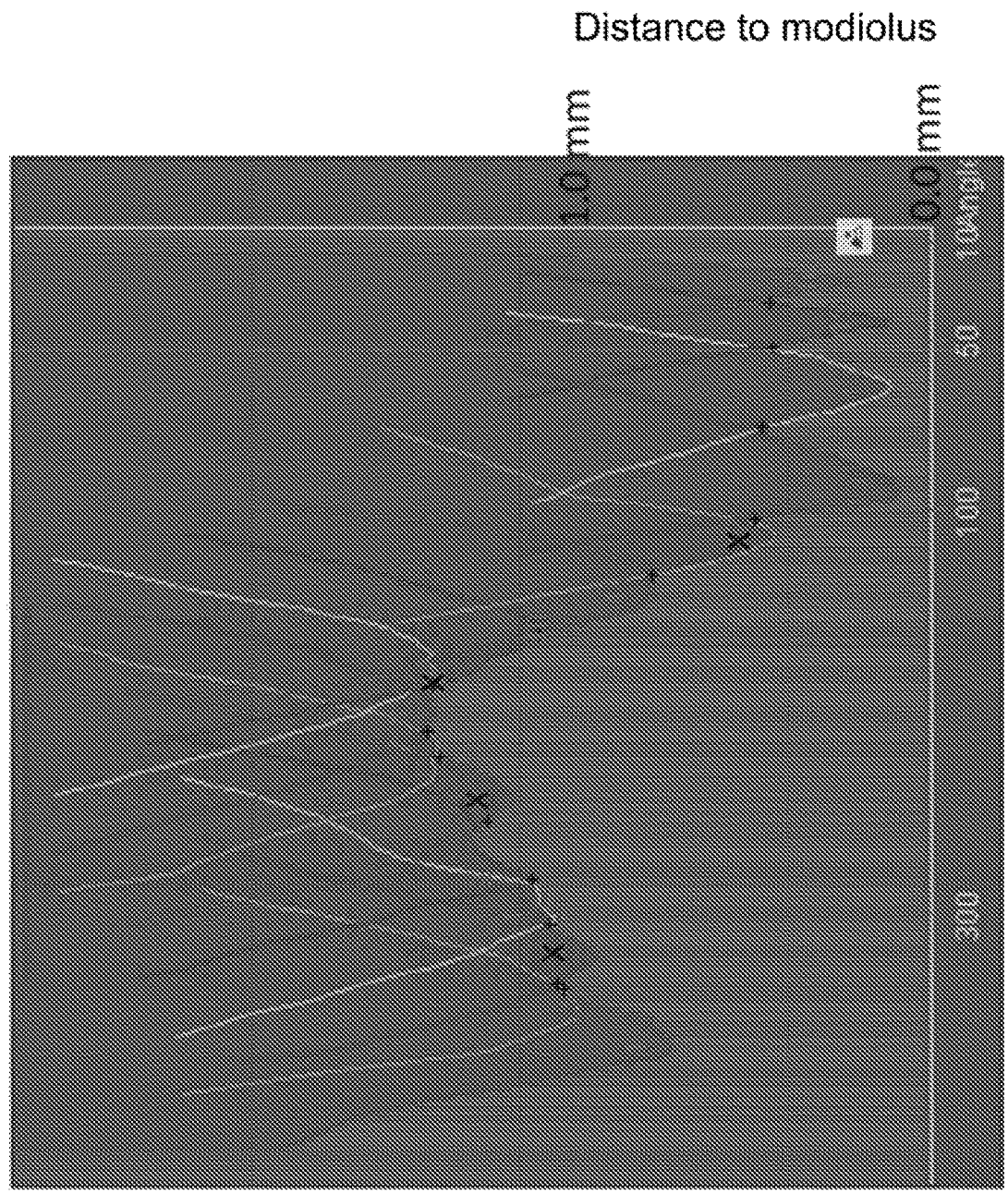
FIG. 6 schematically shows a plot of the DVF curves obtained from a patient processed to select the interfering electrodes to be deactivated according to certain embodiments of the present invention.
Figure 7:
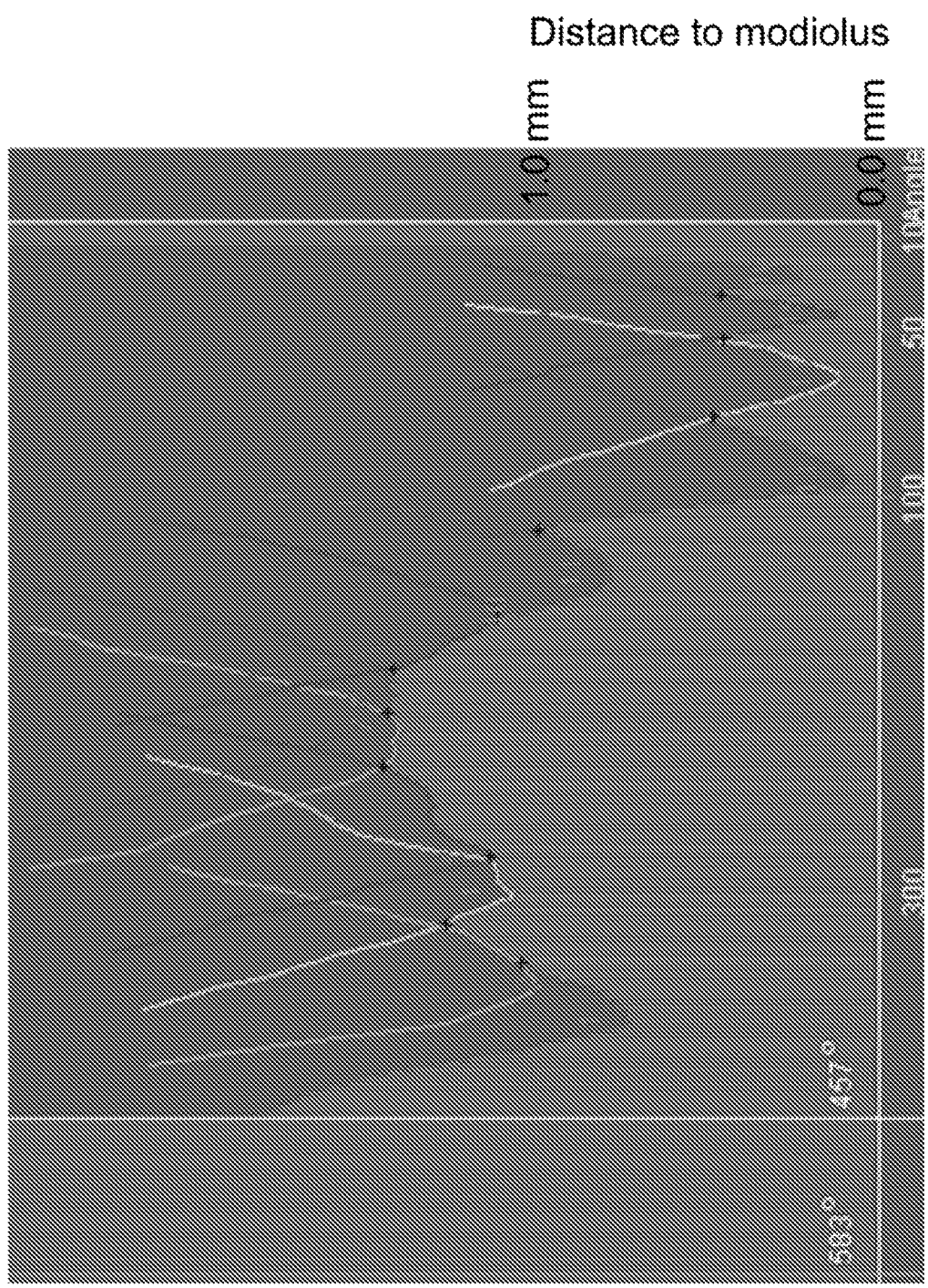
FIG. 7 schematically shows a plot of the DVF curves after deactivating the selected interfering electrodes as shown in FIG. 6 according to certain embodiments of the present invention.

In the experiment for patient #2, a cochlear implant device having an electrode array with 16 electrodes is used to obtain the raw DVF curves. Then the raw DVF curves are processed similarly to select the interfering electrodes to be deactivated. FIG. 6 schematically shows a plot of the DVF curves obtained from a patient processed to select the interfering electrodes to be deactivated according to certain embodiments of the present invention. As shown in FIG. 6, by applying the rules, the electrodes #3, #6, #9 and #12 were selected to be deactivated. This removes the steered channels shown in red above. FIG. 7 schematically shows a plot of the DVF curves after deactivating the selected interfering electrodes as shown in FIG. 6 according to certain embodiments of the present invention.

Results

For both patients in the experiment, their acute response when switching from their clinical, long term use map to the new experimental map was very positive in both cases. Both remarked that the experimental maps sound clearer and louder. This is remarkable as there is a known bias with cochlear implant patients strongly preferring their existing long term maps rather than experimental ones. Quantitative results acquired after long term use (about 4 weeks) of the experimental maps will confirm whether the experimental maps result in improved speech recognition over clinical standard of care.

Experiment Two

Experimental Design

Participants

Certain embodiments of the method are further tested in cochlear implant subjects. In the following experiment, ten adult (7 postlingual) and 2 pediatric CI recipients implanted with the Advanced Bionics (Valencia, Calif.) cochlear implant system and using paired stimulation strategies participated in this study. Average age was 49 years (range: 24-63) for the adult group and 7 years (range: 4-10) for the pediatric group. Participants had at least 6-months experience with the device prior to study enrollment. Average device experience was 3.83 years (range: 1.15 to 13 years) for the adult group and 7 years (range: 2-7.9) for the pediatric group. Four bilateral participants participated with their poorer performing ear. A total of 7 females and 5 males participated. All adult participants scored at least 25 on the mini mental state examination (MMSE), indicating no significant risk of cognitive impairment [14]. Informed consent was obtained from each participant in accordance with the study protocols approved by the local Institutional Review Board.

A repeated-measures, within-participant design was used to compare the participant's current listening program to the experimental IGCIP program. All speech tests were administered in the electric only condition alone as well as in the best aided condition (i.e., bilateral implants, CI+HA). Estimates of spectral resolution were obtained using a spectral modulation detection (SMD) task [15]. Participants were evaluated with these tests at the first testing session with their current listening program and a subsequent session after approximately four weeks use of the IGCIP program.

Electrode Position Detection

The challenges with using a conventional post-op CT scans to localize electrodes relative to the sites they stimulate is (1) that the intracochlear structures (e.g., spiral ganglion cells, etc.) are not well contrasted in conventional CT and (2) artifact from the electrode contacts degrade the image. Because the walls of the cochlea are well defined in pre-op CT [11], developed an approach to use these well-defined features as landmarks to estimate the location of internal cochlear anatomy not well defined in these images. The cochlear implant electrode array is well contrasted in post-op CT, which is registered to the pre-op CT scan for analysis of the spatial relationship between the cochlear implant electrode contacts and the spiral ganglion cells. Further information on the image processing techniques can be found in the reference [11].

Program Creation Process

Once the location of the electrode contacts relative to the sites they stimulate is known, electrode distance-vs-frequency (DVF) curves [11] are used to visualize electrode distance from the modiolus and aid in electrode selection.

Figure 8:
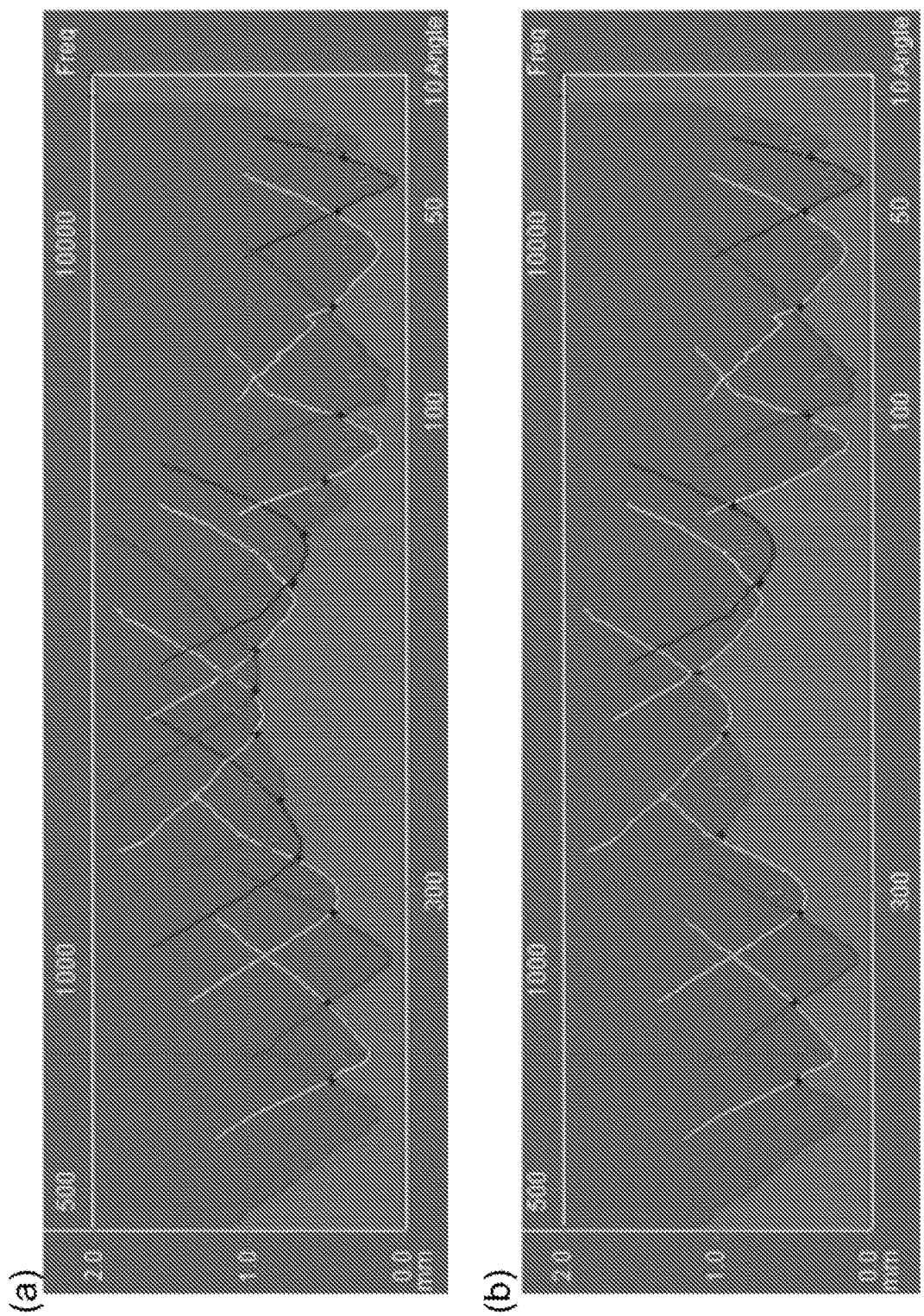
FIG. 8 schematically shows (a) a plot of raw DVF curves obtained from a patient and (b) a plot of the DVF curves after deactivating the selected interfering electrodes according to certain embodiments of the present invention.

FIG. 8 schematically shows (a) a plot of raw DVF curves obtained from a patient and (b) a plot of the DVF curves after deactivating the selected interfering electrodes according to certain embodiments of the present invention. In particular, as shown in FIG. 8, the height of each electrode's DVF curve on the vertical axis represents the distance from the corresponding electrode to spiral ganglion stimulation sites, and the horizontal axis shows the angular depth and characteristic frequency (CF) of those stimulation sites. Interference between neighboring electrodes is identified for electrodes that are farther from the modiolus (higher in the plot) and have curves that have a high degree of overlap (little or no depth of concavity) with their neighbors, e.g., between electrodes 7 and 8 as shown in FIG. 8(a). This indicates the two electrodes are equally close to the same neural sites, and thus a high degree of channel interference is occurring and the electrodes are stimulating many of the same neural sites. In certain embodiments, the rules being used for choosing the interfering electrodes to be deactivated include: (1) keeping the left-most electrode in the plot on to avoid a resulting sound frequency upshift, (2) not leaving any electrode stranded without a neighbor because this would prevent current steering, and (3) deactivating a minimal number of electrodes necessary to ensure that high interference is allowed only with one neighbor of each active electrode. As both neighbors represent a "steered" channel, the last rule ensures that two neighboring steered channels do not have high interference with each other. These rules indicate deactivating electrodes 5, 8, and 11, and as shown in FIG. 8(b), the remaining DVF curves after deactivation are shown.

This procedure was implemented for each subject who participated in the experiment. After deactivation, rate was held constant. Manipulation of upper and lower stimulation levels on individual electrodes was not permitted. If a participant reported a significant change in perceived volume, a global upper stimulation level adjustment was allowed.

Speech Recognition

All stimuli were presented from a single loudspeaker at 0°. Speech recognition in quiet was assessed using one 50-word consonant-nucleus-consonant [16] list and one 20-sentence AzBio list [17] in accordance with the minimum speech test battery (MTSB) protocol [18]. Participants who scored greater than 30% correct in quiet were also tested at a +5 dB signal-to-noise (SNR) ratio using a multi-talker babble. Additionally, speech recognition in noise was assessed with the Bamford-Kowal-Bench Speech-in-Noise (BKB-SIN) test [19]. The BKB-SIN results in a signal-to-noise ratio at which the listener would attain approximately 50% correct. All speech tests were administered in the electric only condition alone as well as in the best aided condition (i.e., bilateral implants, CI+HA).

Spectral Modulation Detection (SMD)

Estimates of spectral resolution were obtained using a spectral modulation detection (SMD) task [15]. Spectral envelope perception as measured by spectral modulation detection (SMD) serves as a psychoacoustic estimate of spectral resolution that is highly correlated with speech understanding [15, 20, 21]. For this study, the quick SMD (QSMD) task [15] is used, which utilizes a 3-interval, forced choice procedure based on a modified method of constant stimuli in which the listener is asked to differentiate a spectrally modulated band of noise from that of a flat spectrum noise. There are a fixed number of trials at each modulation depth and frequency. Each trial is scored as correct or incorrect and spectral resolution is described as the overall percent correct score for the task (chance=33%). The stimulus was created by applying a logarithmically spaced, sinusoidal modulation to the broadband carrier stimulus with a bandwidth of 125-5600 Hz. A total of 60 trials at five modulation depths (10, 11, 13, 14, and 16 dB) and two modulation frequencies (0.5 and 1.0 cycles/octaves) were evaluated. All stimuli were calibrated and presented in the free field at 60 dBA from a single loudspeaker. SMD was tested only in the e-alone configuration (i.e., acoustic hearing ears were occluded with a foam EAR plug).

Results

Figure 9B:
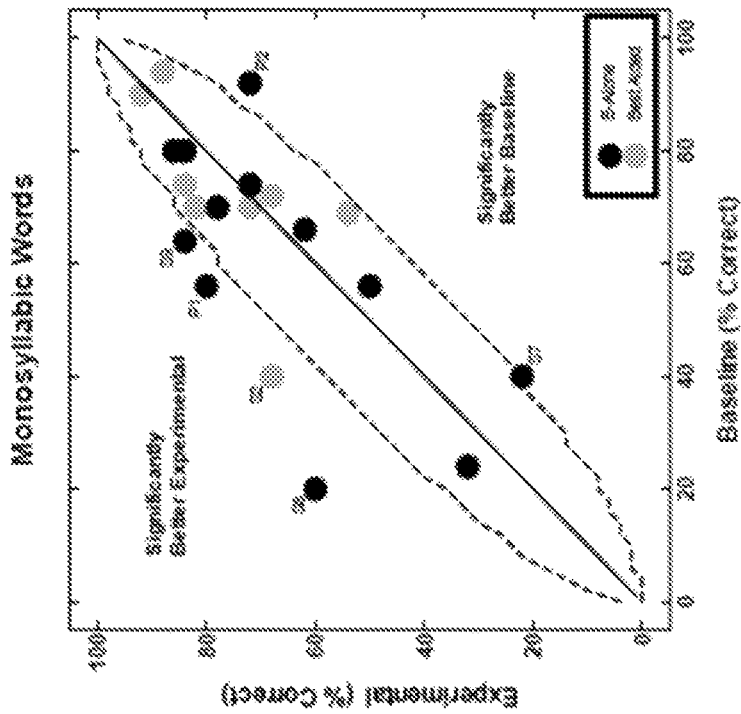
FIG. 9B schematically shows hearing performance scores of monosyllabic words with the experimental steering compatible map vs the baseline map according to certain embodiments of the present invention.
Figure 9A:
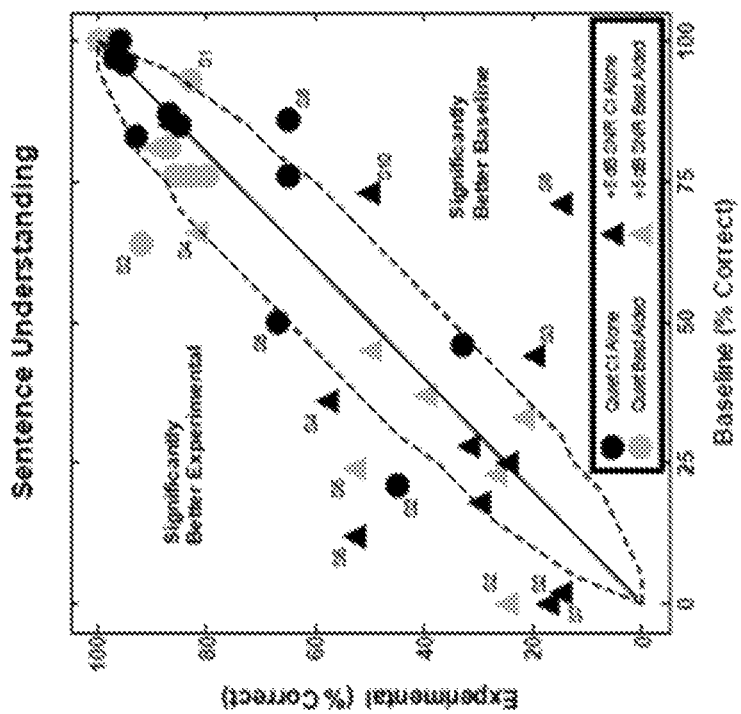
FIG. 9A schematically shows hearing performance scores of sentence understanding with the experimental steering compatible map vs the baseline map according to certain embodiments of the present invention.
Figure 9D:
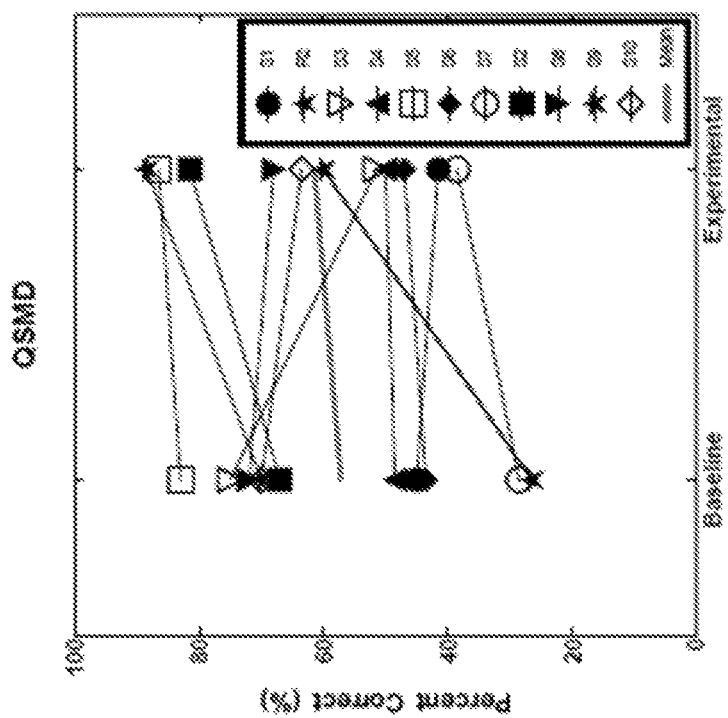
FIG. 9D schematically shows hearing performance scores of QSMD with the experimental steering compatible map vs the baseline map according to certain embodiments of the present invention.
Figure 9C:
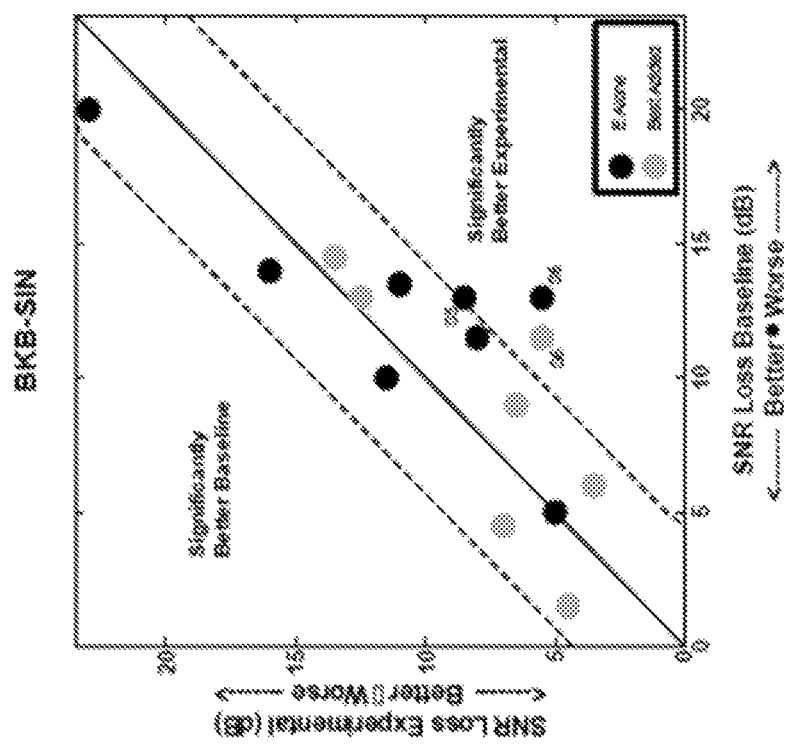
FIG. 9C schematically shows hearing performance scores of BKB-SIN with the experimental steering compatible map vs the baseline map according to certain embodiments of the present invention.
Figures 10A, 10B:
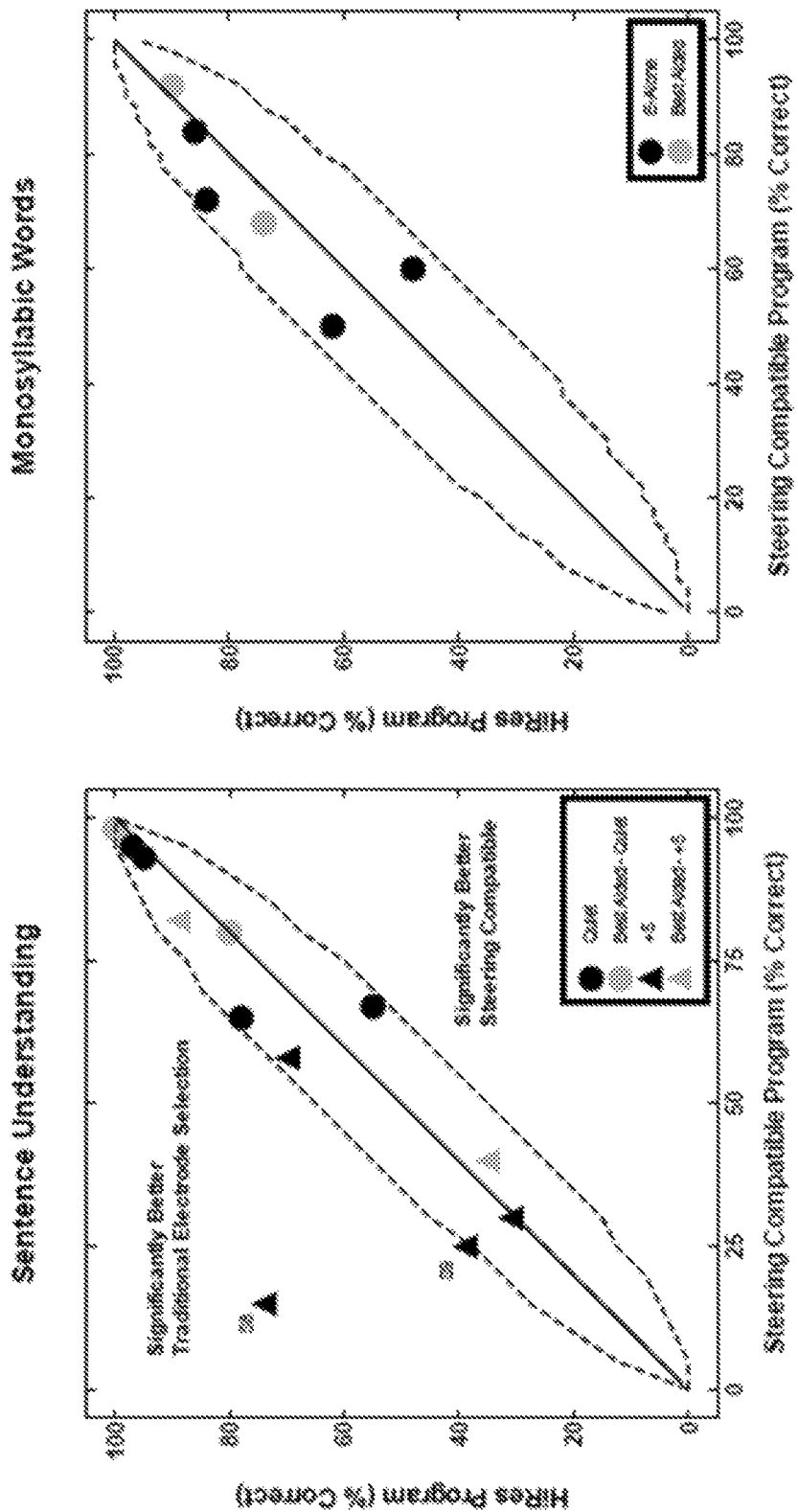
FIG. 10A schematically shows hearing performance scores of sentence understanding with the experimental steering compatible map vs the baseline map according to certain embodiments of the present invention.
FIG. 10B schematically shows hearing performance scores of monosyllabic words with the experimental steering compatible map vs the baseline map according to certain embodiments of the present invention.
Figure 10D:
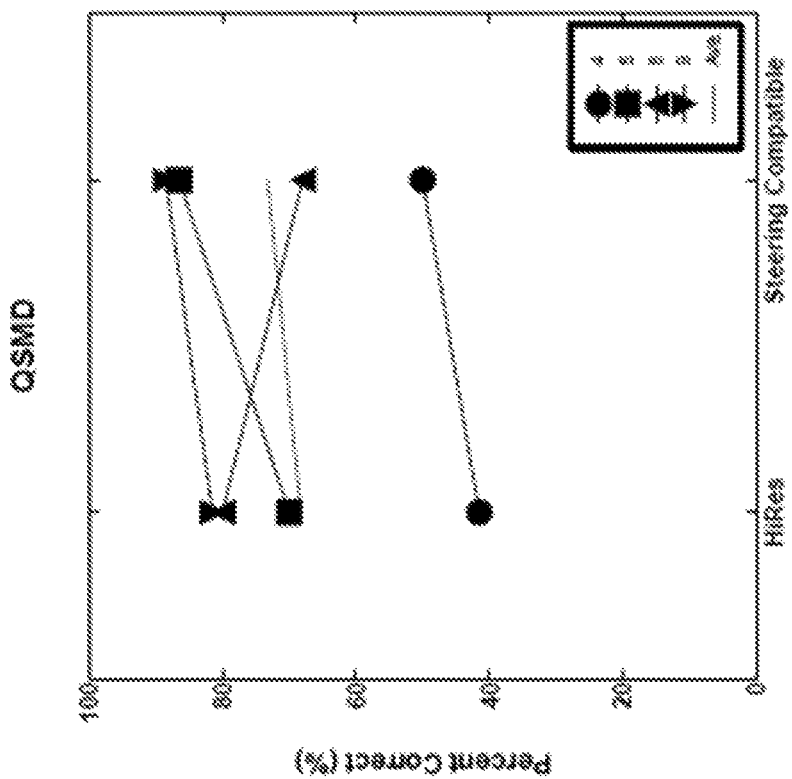
FIG. 10D schematically shows hearing performance scores of QSMD with the experimental steering compatible map vs the baseline map according to certain embodiments of the present invention.
Figure 10C:
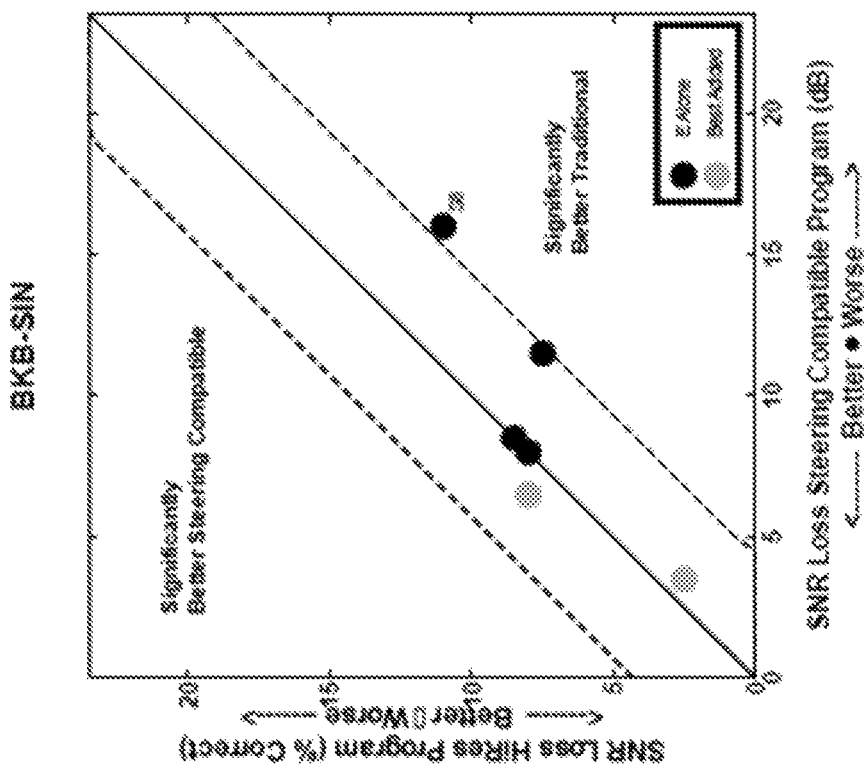
FIG. 10C schematically shows hearing performance scores of BKB-SIN with the experimental steering compatible map vs the baseline map according to certain embodiments of the present invention.

FIGS. 9A to 9D respectively show the hearing performance scores of sentence understanding, monosyllabic words, BKB-SIN and QSMD with the experimental steering compatible map vs the baseline map according to certain embodiments of the present invention. Specifically, individual hearing performance scores for the baseline program (x-axis) and IGCIP with current steering (y-axis) program are shown in FIGS. 9A-9C. The dashed lines outline the 95% confidence interval for respective test materials. Data points falling outside this region are considered to be significantly different between the two programs for a given participant. The solid diagonal represents no difference between programs.

AzBio sentence scores are shown in FIG. 9A for implant ear alone and the best aided condition in quiet and in noise. Sentence scores falling outside the 95% confidence interval for AzBio sentence materials are considered to be significantly different between the two programs for a given participant (Spahr et al., 2012). One individual scored worse in quiet in the best aided condition, however, caution should be used interpreting two of these data points located in the top right of the plot as real differences as the function is compressed at the extremes due to floor and ceiling effects (Spahr et al., 2012). Three individuals scored worse with the IGCIP program in noise with the CI alone. One individual scored worse in quiet and in noise for the CI alone condition. One individual did better in quiet and in noise in the CI alone and best-aided condition with the IGCIP program. One individual performed better in quiet in the CI alone condition with the IGCIP program. One individual scored better in noise with the CI alone and in the best-aided condition. One individual scored better with the IGCIP program in quiet with their CI alone. Three individuals performed better in noise in the electric only condition with the IGCIP program. Two individuals did better with the IGCIP program in the best-aided condition. One individual (S2) scored significantly better on all tests (quiet, noise, CI alone and best-aided).

As shown in FIG. 9B, a binomial distribution model for monosyllabic word recognition with 50 words [22] revealed significant differences in word recognition between the two programs for 6 individuals. Four individuals score significantly better (3 in the electric alone condition and 1 best aided) and 2 significantly worse in the electric alone condition.

As shown in FIG. 9C, two individuals scored significantly better on the BKB-SIN with the IGCIP program. No other individual differences were observed. No significant group differences were observed on our measure of spectral resolution. However, improvements were observed for 8 individuals. Overall, the number of scores that represent improvement is approximately double the number of those that do not. A total of 17 scores represent improvements that are statistically significant on the individual level.

Several participants (n=4) previously participated in the 2014 study were brought back to evaluate a steering compatible version of IGCIP. These results can be seen in FIGS. 10A to 10D, where individual hearing performance scores for the traditional HiRes IGCIP program are shown on the x-axis and the IGCIP with current steering results are shown on the y-axis. One individual scored significantly better in the CI alone condition in noise with the traditional IGCIP implementation (HiRes IGCIP). This individual has a history of fluctuating performance due to day to day changes in sound quality likely secondary to Ménière's disease diagnosis.

At the end of the study 10 of 12 subjects elected to keep one of the IGCIP programs as their 'everyday' program. Eight kept the steered program as their 'everyday' program, two returned to their HiRes IGCIP program, and two returned to their baseline program.

In sum, the paired electrode IGCIP strategy proposed can yield significant improvements in speech understanding in quiet, in noise, on measures of spectral resolution, as well as improvements in subjective sound quality. Sixty-seven percent of participants (8/12) showed significant improvement on at least one test measure. The paired electrode IGCIP strategy yielded equivalent results when compared to HiRES IGCIP in four individuals who participated in both studies. Eight of 12 participants kept the steered program as their 'everyday' program, and two returned to their HiRes IGCIP program.

In a further aspect, the present disclosure is related to a non-transitory computer readable medium storing computer executable code. The computer executable code, when executed at one or more processor, may perform the method as described above. In certain embodiments, the non-transitory computer readable medium may include, but not limited to, any physical or virtual storage media.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1]. [NID14] National Institute on Deafness and Other Communication Disorders, "Cochlear Implants," No. 11-4798, 2014.

[Bus08] Buss E, Pillsbury H C, Buchman C A, Pillsbury C H, Clark M S, Haynes D S, Labadie R F, Amberg S, Roland P S, Kruger P, Novak M A, Wirth J A, Black J M, Peters R, Lake J, Wackym P A, Firszt J B, Wilson B S, Lawson D T, Schatzer R, S. DHP, Barco A L: Multicenter U.S. Bilateral med-el cochlear implantation study: Speech perception over the first year of use. Ear Hear 2008; 29:20-32.

[3]. [Dor09] Dorman M F, Yost W, Wilson B S, Gifford R H: Speech perception and sound localization by adults with bilateral cochlear implants. Seminars in Hearing 2009; 32:73-89.

[4]. [Gif08] Gifford R H, Shallop J K, Peterson A M. (2008). Speech Recognition Materials and Ceiling Effects: Considerations for Cochlear Implant Programs. Audiol Neurotol, 13:193-205.

[5]. [Gif14a] Gifford R H, Dorman M F, Sheffield S W, Teece K, Olund A P.
"Availability of binaural cues for bilateral cochlear implant recipients and bimodal listeners with and without hearing preservation." Audiol Neurotol. 2014; 19(1):57-71

[6]. [Lit06] Litovsky R Y, Parkinson A, Arcaroli J, Sammeth C: Simultaneous bilateral cochlear implantation in adults: A multicenter clinical study. Ear Hear 2006; 27:714-730.

[7]. [Hol13] Holden L K, Finley C C, Firszt J B, Holden T A, Brenner C, Potts L G, Gotter B D, Vanderhoof S S, Mispagel K, Heydebrand G, Skinner M W., "Factors affecting open-set word recognition in adults with cochlear implants," Ear Hear. 34(3):342-60, 2013.

[8]. [Wan14] Wanna, G. B., Noble J. H., Carlson, M. L., Gifford, R. H., Dietrich, M. S., Haynes, D. S. Dawant, B. M., and Labadie, R. F., "Impact of Electrode Design and Surgical Approach on Scalar Location and Cochlear Implant Outcomes," Laryngoscope, vol. 124(S6), pp. S1-7, 2014.

[9]. [Wan15] Wanna G B, Noble J H, Gifford R H, Dietrich M S, Sweeney A D, Zhang D, Dawant B M, Rivas A, Labadie R F. "Impact of Intrascalar Electrode Location, Electrode Type, and Angular Insertion Depth on Residual Hearing in Cochlear Implant Patients: Preliminary Results." Otol Neurotol. 36(8):1343-8, 2015.

[10]. [Sta07] Stakhovskaya O, Spridhar D, Bonham B R Leake P A. Frequency Map for the Human Cochlear Spiral Ganglion: Implications for Cochlear Implants. Journ. Assoc. Res. Otol. 8, 2007: 220-233.

[11]. [Nob13] Noble J H, Labadie R F, Gifford R H, Dawant B M, "Image-guidance enables new methods for customizing cochlear implant stimulation strategies," IEEE Trans Neural Syst Rehabil Eng. vol. 21(5):820-9, 2013.

[12]. [Nob14] Noble J H, Gifford R H, Hedley-Williams A J, Dawant B M, and, Labadie R F, "Clinical evaluation of an image-guided cochlear implant programming strategy," Audiology & Neurotology, vol. 19, pp. 400-11, 2014.

[13]. [Koc14] Koch D B I, Quick A, Osberger M J, Saoji A, Litvak L. "Enhanced hearing in noise for cochlear implant recipients: clinical trial results for a commercially available speech-enhancement strategy." Otol Neurotol. 2014 June; 35(5):803-9.

[14]. [Fol75] Folstein M F, Folstein S E, McHugh P R. Mini-mental state. A practical method for grading the cognitive state of patients for the clinician. J Psychiatr Res 1975; 12:189-198.

[15]. [Gif14b] Gifford R H, Hedley-Williams A, Spahr A J. Clinical assessment of spectral modulation detection for cochlear implant recipients: a non-language 480 based measure of performance outcomes. Int J Audiol 2014; 53(3):159-64.

[16]. [Pet62] Peterson G E, Lehiste I. (1962). Revised CNC lists for auditory tests. J Speech Hear Disord. 27:62-70.

[17]. [Spa12] Spahr A. J., Dorman M. F., Litvak L. M., Van Wie S., Gifford R. H., Loizou P. C., Loiselle L. M., Oakes T., Cook S., "Development and validation of the AzBio sentence lists," Ear Hear. 33(1): 112-7, 2012.

[18]. [MTSB] MSTB: The New Minimum Speech Test Battery for Adult Cochlear Implant Users. Available at: http://auditorypotential.com/MSTB.html. Accessed Dec. 10, 2015.

[19]. [Ben79] Bench J., Kowal A., Bamford J., "The BKB (Bamford-Kowal-Bench) sentences lists for partially-hearing children," Br. J. Audiol. 13: 108-12, 1979.

[20]. [Lit07] Litvak L M, Spahr A J, Saoji A A, Fridman G Y. Relationship between perception of spectral ripple and speech recognition in cochlear implant and vocoder listeners. J Acoust Soc Am 2007; 122: 982-991.

[21]. [Sao09] Saoji A A, Litvak L M, Spahr A J, Eddins D A. Spectral modulation detection and vowel and consonant identifications in cochlear implant listeners. J Acoust Soc Am 2009; 126 (3): 955-8.

[22]. [Tho78] Thornton A R, Raffin M J. Speech-discrimination scores modeled as a binomial variable. J Speech Hear Res 1978; 21:507-518.

What is claimed is:

1. A method for performing current steering compatible image-guided cochlear implant (CI) electrode deactivation, comprising:
   (a) obtaining, for a plurality of electrodes of a cochlear implanted electrode array of a CI a plurality of distance-vs-frequency (DVF) curves, wherein each of the DVF curves corresponds to one of the electrodes of the cochlear implanted electrode array;
   (b) performing an analysis on the DVF curves to identify a plurality of interfering electrodes from the electrodes, wherein each of the interfering electrodes has an interference with at least one other electrode; and
   (c) selecting and deactivating, based on a plurality of rules, at least one of the interfering electrodes.

2. The method of claim 1, wherein the DVF curves are provided on a plot to visualize distances of the electrodes, wherein the plot has a horizontal axis showing an angular depth and a characteristic frequency (CF) of the neural regions, and a vertical axis showing a distance from the electrodes to corresponding spiral ganglion stimulation sites.

3. The method of claim 2, wherein the interfering electrodes are identified from the electrodes based on positions of the electrodes relative to neural regions stimulated by the electrodes, and an overlapping degree of each of the corresponding neural regions of the electrodes, wherein each of the electrodes corresponds to one of the neural regions.

4. The method of claim 3, wherein the positions of the electrodes relative to the neural regions are determined by locations of the DVF curves on the vertical axis of the plot, wherein for each of the electrodes, the position of the electrode is farther from the corresponding neural region when the corresponding DVF curve of the electrode is higher on the plot.

5. The method of claim 3, wherein the overlapping degree of each of the corresponding neural regions of the electrodes is estimated by depths of concavity between the DVF curves on the plot, wherein for each of the DVF curves, the overlapping degree is high when the DVF curve has little to no depth of concavity with neighboring DVF curves on the plot.

6. The method of claim 2, wherein the rules comprise:
keeping the electrode having a corresponding DVF curve located at a left-most location on the plot to avoid a resulting sound frequency upshift;
avoiding leaving any of the electrodes stranded without a neighboring electrode; and
deactivating a minimal number of the interfering electrodes to ensure that high interference is allowed only for each of the electrodes with one of its neighboring electrodes.

7. A method for customizing cochlear implant stimulation using a current steering compatible image-guided cochlear implant programming (IGCIP) strategy, comprising:
configuring the plurality of electrodes of cochlear implant electrode array using the method of claim 1.

8. A system for performing current steering compatible image-guided cochlear implant (CI) electrode deactivation, comprising:
a CI device comprising a cochlear implanted electrode array having a plurality of electrodes; and
at least one computing device having one or more processors and a storage device storing computer executable code, wherein the computer executable code, when executed at the one or more processors, is configured to perform functions comprising:
(a) obtaining, for the electrodes of the cochlear implanted electrode array of the CI device, a plurality of distance-vs-frequency (DVF) curves, wherein each of the DVF curves corresponds to one of the electrodes;
(b) performing an analysis on the DVF curves to identify a plurality of interfering electrodes from the electrodes, wherein each of the interfering electrodes has an interference with at least one other electrode; and
(c) selecting and deactivating, based on a plurality of rules, at least one of the interfering electrodes.

9. The system of claim 8, wherein the functions further comprise:
providing the DVF curves on a plot to visualize distances of the electrodes, wherein the plot has a horizontal axis showing an angular depth and a characteristic frequency (CF) of the neural regions, and a vertical axis showing a distance from the electrodes to corresponding spiral ganglion stimulation sites.

10. The system of claim 9, wherein the interfering electrodes are identified from the electrodes based on positions of the electrodes relative to neural regions stimulated by the electrodes, and an overlapping degree of each of the corresponding neural regions of the electrodes, wherein each of the electrodes corresponds to one of the neural regions.

11. The system of claim 10, wherein the positions of the electrodes relative to the neural regions interfering electrodes are determined by locations of the DVF curves on the vertical axis of the plot, wherein for each of the electrodes, the position of the electrode is farther from the corresponding neural region when the corresponding DVF curve of the electrode is higher on the plot.

12. The system of claim 10, wherein the overlapping degree of each of the corresponding neural regions of the electrodes is estimated by depths of concavity between the DVF curves on the plot, wherein for each of the DVF curves, the overlapping degree is high when the DVF curve has little to no depth of concavity with neighboring DVF curves on the plot.

13. The system of claim 9, wherein the rules comprise:
keeping the electrode having a corresponding DVF curve located at a left-most location on the plot to avoid a resulting sound frequency upshift;
avoiding leaving any of the electrodes stranded without a neighboring electrode; and
deactivating a minimal number of the interfering electrodes to ensure that high interference is allowed only for each of the electrodes with one of its neighboring electrodes.

14. A method for customizing cochlear implant stimulation of a living using a current steering compatible image-guided cochlear implant programming (IGCIP) strategy, comprising:
configuring the plurality of electrodes of the cochlear implant electrode array using the system of claim 8.

15. A non-transitory computer-readable medium storing computer executable code, wherein the computer executable code, when executed at one or more processors, causes a system to perform functions for performing current steering compatible image-guided cochlear implant (CI) electrode deactivation, the functions comprising:
(a) obtaining, for a plurality of electrodes of a cochlear implanted electrode array of a CI device a plurality of distance-vs-frequency (DVF) curves, wherein each of the DVF curves corresponds to one of the electrodes of the cochlear implanted electrode array;
(b) performing an analysis on the DVF curves to identify a plurality of interfering electrodes from the electrodes, wherein each of the interfering electrodes has an interference with at least one other electrode; and
(c) selecting and deactivating, based on a plurality of rules, at least one of the interfering electrodes.

16. The non-transitory computer-readable medium of claim 15, wherein the functions further comprise:
providing the DVF curves on a plot to visualize distances of the electrodes, wherein the plot has a horizontal axis showing an angular depth and a characteristic frequency (CF) of the neural regions, and a vertical axis showing a distance from the electrodes to corresponding spiral ganglion stimulation sites.

17. The non-transitory computer-readable medium of claim 16, wherein the interfering electrodes are identified from the electrodes based on positions of the electrodes relative to neural regions stimulated by the electrodes, and an overlapping degree of each of the corresponding neural regions of the electrodes, wherein each of the electrodes corresponds to one of the neural regions.

18. The non-transitory computer-readable medium of claim 17, wherein the positions of the electrodes relative to the neural regions are determined by locations of the DVF curves on the vertical axis of the plot, wherein for each of the electrodes, the position of the electrode is farther from the corresponding neural region when the corresponding DVF curve of the electrode is higher on the plot.

19. The non-transitory computer-readable medium of claim 17, wherein the overlapping degree of each of the corresponding neural regions of the electrodes is estimated by depths of concavity between the DVF curves on the plot, wherein for each of the DVF curves, the overlapping degree is high when the DVF curve has little to no depth of concavity with neighboring DVF curves on the plot.

20. The non-transitory computer-readable medium of claim 16, wherein the rules comprise:
   keeping the electrode having a corresponding DVF curve located at a left-most location on the plot to avoid a resulting sound frequency upshift;
   avoiding leaving any of the electrodes stranded without a neighboring electrode; and
   deactivating a minimal number of the interfering electrodes to ensure that high interference is allowed only for each of the electrodes with one of its neighboring electrodes.

* * * * *